United States Patent [19]

Lieber

[11] Patent Number: 4,838,272
[45] Date of Patent: Jun. 13, 1989

[54] METHOD AND APPARATUS FOR ADAPTIVE CLOSED LOOP ELECTRICAL STIMULATION OF MUSCLES

[75] Inventor: Richard L. Lieber, Carlsbad, Calif.

[73] Assignee: The Regents of the University of California, Berkeley, Calif.

[21] Appl. No.: 87,470

[22] Filed: Aug. 19, 1987

[51] Int. Cl.[4] .................... A61N 000/00; H05G //00
[52] U.S. Cl. .................................................. 128/421
[58] Field of Search .............. 128/421, 422, 423 W, 128/25 B, 25 R

[56] References Cited

U.S. PATENT DOCUMENTS

| | | | |
|---|---|---|---|
| 4,165,750 | 8/1979 | Aleev et al. | 128/422 |
| 4,177,819 | 10/1979 | Kofsky et al. | 128/422 |
| 4,236,528 | 10/1980 | Stanec et al. | 128/741 |
| 4,408,609 | 10/1983 | Axelgaard | 128/421 |
| 4,492,233 | 1/1985 | Petrofsky et al. | 128/421 |
| 4,499,900 | 2/1985 | Petrofsky et al. | 128/423 |
| 4,556,214 | 12/1985 | Petrofsky et al. | 272/117 |
| 4,569,352 | 2/1986 | Petrofsky et al. | 272/117 |
| 4,586,495 | 5/1986 | Petrofsky | 128/25 B |
| 4,598,713 | 7/1986 | Hansjürgens et al. | 128/422 |

OTHER PUBLICATIONS

Fundamentals Handbook of Electrical and Computer Engineering, vol. II, Wiley-Interscience Publication, edited by Chang 1983.

Computer Controlled Walking in the Paralized Individual, by J. S. Petrofsky and C. A. Phillips, appearing in the Journal of Neurological and Orthopedic Surgery, vol. 4, No. 2, Jul. 1983.

*Primary Examiner*—Francis Jaworski
*Assistant Examiner*—George Manuel
*Attorney, Agent, or Firm*—Brown, Martin, Haller & McClain

[57] ABSTRACT

A method and apparatus for strengthening skeletal muscles through maximizing muscle tension in which electrical stimulation signals are applied to the selected muscles at a predetermined frequency, pulse width, and amplitude, and work output by the muscles in response to stimulation signals is determined over a fixed period of time. The work output is compared to a defined value which can be a target value or a value measured during a previous stimulation period. The amount of electrical energy coupled into the muscles by the stimulation signals is varied in response to the results of the comparison in order to maximize the amount of work output by the muscles during a treatment period. This is accomplished by adjusting the frequency or pulse width during stimulation treatment in response to the work output measured.

24 Claims, 4 Drawing Sheets

METHOD AND APPARATUS FOR ADAPTIVE CLOSED LOOP ELECTRICAL STIMULATION OF MUSCLES

BACKGROUND OF THE INVENTION

1. Field of the Invention

The present invention relates to apparatus for electrically stimulating muscle activity and more particularly to an apparatus and method for functional electrical stimulation of preselected muscles for tensioning the muscles to improve strength. The invention further relates to an apparatus and method for stimulating muscles more efficiently according to muscle type and work history.

2. Background of the Invention

The use of electrical pulses or signals to induce muscle contractions and, thus, stimulate muscle movement or exercise is well known in the medical sciences. A variety of methods and apparatus for stimulating muscle movement have been developed especially for application in the area of locomotion for paralyzed limbs. Along this line, there have been a number of attempts to develop apparatus that will allow individuals suffering from paralysis or various neurological or muscular disorders to walk or motivate otherwise non-functional muscles in a controlled manner.

At the same time, it is known that electrical stimulation is useful for general exercise of otherwise functional muscles for improving muscle tone or strength. Many applications exist for a method of improving muscle strength or tone to counter atrophy from disuse that is secondary to trauma or associated indirectly with some type of incapacitation. This includes long term bed rest, long term joint immobility do to fractures or fatiguing illnesses, or other bodily injuries or illnesses that restrict muscular exercise and use for prolonged periods.

It is also fairly well understood that general muscle strength, condition, and tone has a significant impact on overall health which is often undermined by inadequate exercise. Electrical stimulation may serve as an adjunct, in an otherwise healthy patient, to self induced muscular exercise to improve muscle strength. This is especially important in special applications such as in sports medicine where specific muscle groups can be strengthened to decrease the impact of injuries or surgery when traditional exercise is not possible.

Examples of the devices and protocols that have been developed for use in muscle therapy, training, motivation, control, or exercise are disclosed in U.S. Pat. Nos. 4,165,750, 4,177,819, 4,492,233 and 4,569,352.

U.S. Pat. No. 4,165,750, issued to Aleev et al., teaches a basic muscle stimulation device for use in bioelectrically controlled muscle stimulation. The stimulation device utilizes an oscillator circuit for generating an electrical signal at a frequency which stimulates muscular activity in a patient. This patent also discloses the dependence of the lower and upper amplitude limits of stimulation signals on specific muscle types and patients.

U.S. Pat. No. 4,177,819, issued to Kofskey et al, discloses a microprocessor controlled stimulation circuit which generates bursts of 2000-3000 Hertz signals of 2-20 second duration at 2-50 second intervals. The stimulating waveform increases and decreases in amplitude at the beginning and end of pulse periods and can be interrupted by no-load/overload sensors. The circuitry employs microprocessor technology and digital electronics control elements along with analog power amplifiers to implement the desired pulse pattern.

U.S. Pat. No. 4,492,233 further illustrates the use of transformers and high voltage transistors to drive electrodes at high voltages on the order of 300 volts maximum from digital input signals.

Aside from the limited application to muscle movement of paralyzed or incapacitated patients, the stimulators of these patents employ fixed stimulation signal energies, that is, frequencies or pulse widths, during given treatment periods. Changes in stimulation parameters during exercise, if any, are limited to signal amplitude and duty cycle. In some protocols, as disclosed in *Computer Controlled Walking in the Paralyzed Individual*, by J. S. Petrofsky and C. A. Phillips, Journal of Neurological and Orthopedic Surgery, Vol. 4, No. 2, July 1983, the relative position of joint members associated with the muscles are detected in an attempt to correlate stimulation with muscle motion but the work output is not directly measured or accounted for.

However, the above approaches do not cause muscles to exert maximum tension over a prolonged period of time. To achieve the maximum muscle tension or work during a treatment regime requires knowledge of variations in muscle properties during stimulation. The prior approaches, even when utilizing position sensitive feedback systems, do not measure actual muscle properties to determine the control parameters which account for time and stimulation dependent changes. This leads to such effects as early onset of fatigue on one hand or insufficient stimulation on the other, either of which prevents full and useful exercise. Without a properly balanced tension on the muscle over a prolonged treatment cycle, the muscle is not receiving maximum benefit and the process is inefficient.

The above approaches to muscle stimulation also suffer from the drawback that in a patient operated mode, they do not prevent over-stimulation that can cause muscle or point damage. At the same time, there is no provision for insuring patient compliance in terms of length of treatment or minimum muscle work levels. The prior art apparatus, therefore, requires extensive monitoring by a physician or trained personnel to assure proper use.

What is needed is a method and apparatus for exercising muscles through the application of functional electrical stimulation which achieves a maximum muscle tension dependent upon the current state of the muscle operating properties and, therefore, increased muscle strength through induced exercise. It would desirable to have an electrical stimulation exercise device that automatically adjusts to muscle properties and exercising conditions to assure proper treatment protocol and improved safety.

SUMMARY

With the above drawbacks and shortcomings of the art in mind, it is an object of the present invention to stimulate muscles in a more efficient manner commensurate with the fatigue rates and the output force exerted by the muscles.

It is one purpose of the present invention to provide a method of stimulating muscle movement or contractions that automatically adjusts for muscle fatigue in order to prolong exercise.

It is another purpose of the present invention to provide a method and apparatus for exercising muscles that automatically adjusts signal parameters so that patient compliance is assured and patient progress is enhanced.

It is an advantage of the present invention that it provides a method and apparatus for exercising muscles that efficiently stimulates different types of muscles at differing rates.

It is another advantage of the present invention that it provides an apparatus for exercising muscles that automatically adjusts stimulation signal parameters to fit muscle properties to maintain safe operation for each patient.

These and other advantages, purposes, and objects are realized in a method for strengthening skeletal muscles in which a stimulation signal is applied to the selected muscles at a predetermined frequency, pulse width, and amplitude and the work performed by the muscles in response to the stimulation signal is determined over a fixed period of time. The work performed is compared to a predefined work output value which can be a target value or a value measured during a previous stimulation period. The energy transferred to the muscles by the stimulation signals is varied by a control means in response to increases and decreases in work performed relative to the predefined value.

In further aspects of the invention, the work performed is determined by measuring torque or Electromyogram (EMG) signals generated by the muscles during stimulation and integrating the torque or EMG over a predetermined time interval to yield a work value. The stimulation signal is applied to the muscles at a frequency in the range of about 10 to 100 Hertz which is either incremented or decremented in steps of about 4–6 Hertz depending upon increased or decreased torque output from the muscles respectively. Alternatively, the frequency remains fixed and the pulse width is increased or decreased accordingly to alter the energy coupled into the muscles.

The work performed can be compared to a predefined value by storing the predefined value in a memory storage means within the control means and introducing that value and newly integrated torque or EMG values into a comparator stage in the control means. Alternatively, the work performed is compared to the work performed during previous time periods by storing the integrated value for each N−1 period in the control means and then comparing it with the integrated value for the Nth period. The frequency of the stimulation signal is incremented or decremented by a fixed step in response to increases or decreases, respectively, in work as between adjacent periods.

To implement the method of the present invention, an apparatus is provided having stimulation pulse means for generating pulses of electrical signals at predetermined frequencies and pulse widths to which the muscles are sensitive and using a control means to control the duty cycle. Work detection means, preferably in the form of torque or EMG transducers, is secured adjacent to the joint on which the muscles of interest insert and generates an output indicative of instantaneous work or force exerted by the muscles. The work detection means provides an output value of the work performed over a fixed time interval which is then compared to at least one previously accumulated value. The control means alters the output frequency, or pulse width, of the stimulation signals in response to variations in the work performed.

In further aspects of the apparatus of the present invention, a synchronization means is connected in series with the torque or EMG transducer for gating the output signal of the transducer at predetermined time intervals. An integration means connected in series with the synchronization means receives the transducer output and integrates the magnitude thereof over a fixed interval so as to produce an integrand representative of work exerted by the muscles. This integrand is then compared to a predefined value and the stimulation frequency varied accordingly.

The work output by the muscles along with the stimulation signal parameters can be stored within the control means or associated support elements and retrieved at a later time to show implementation of the actual treatment protocol so that records of user progress can be maintained or displayed.

BRIEF DESCRIPTION OF THE DRAWINGS

The novel features of the present invention may be better understood from the accompanying description when taken in conjunction with the accompanying drawings in which like characters refer to like parts and in which:

FIG. 3b is a graphic presentation of an idealized curve for matching the typical data depicted in FIG. 3a.

DETAILED DESCRIPTION OF A PREFERRED EMBODIMENT

The method and apparatus of the present invention provide functional electrical stimulation of muscles for increasing muscle strength through long term muscle work or activity. This is accomplished in the present invention by varying the frequency of an applied stimulation signal in response to the work or torque exerted by the stimulated muscles so that as the work increases the frequency increases and as the work decreases the frequency decreases over a predetermined exercise period.

Figure 1:
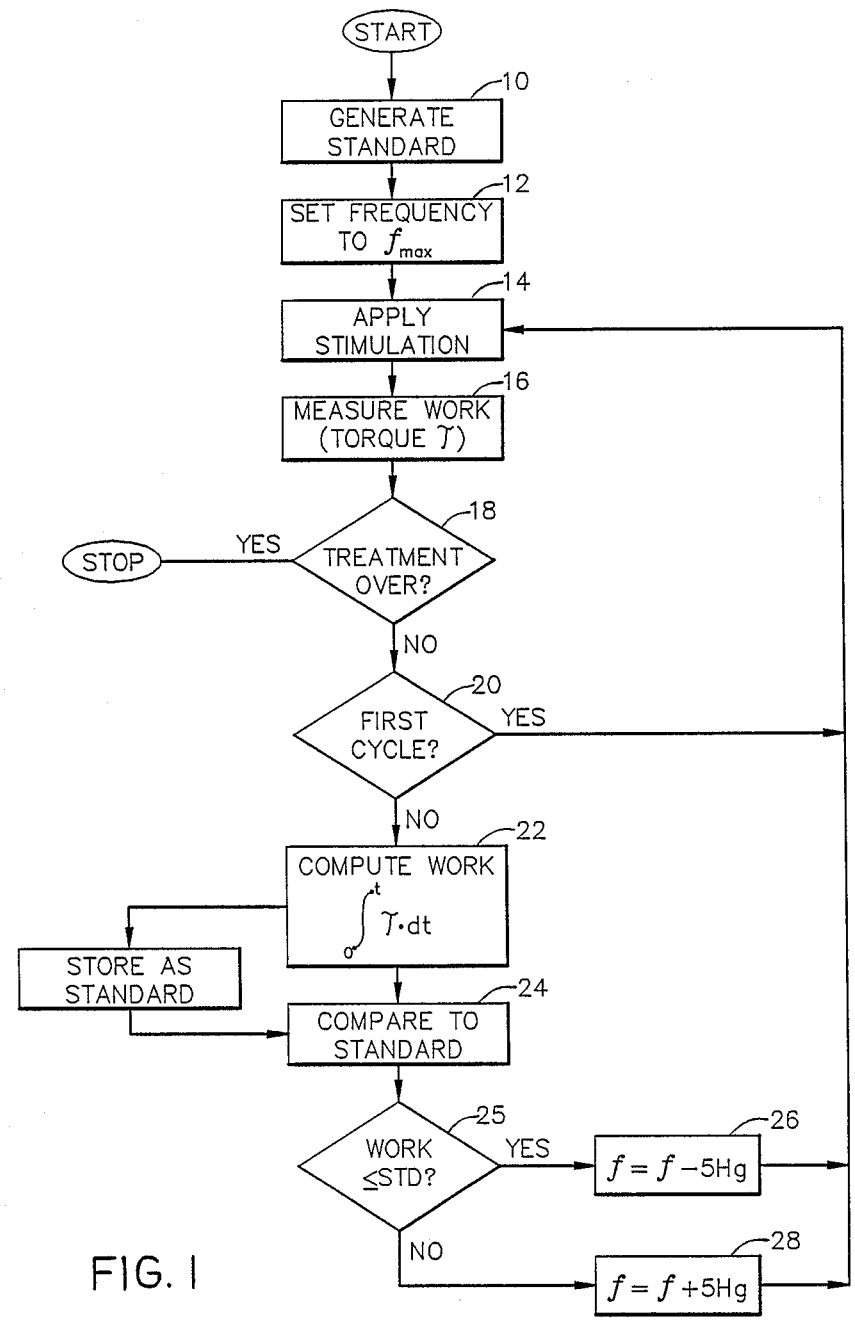
FIG. 1 illustrates a flow chart of the steps to accomplish the method of the present invention.

The steps utilized to implement the method of the present invention are illustrated in flow chart form in FIG. 1. In FIG. 1, step 12 illustrates that, as in any stimulation protocol, the frequency of operation for the stimulation signals must be set along with various other stimulation parameters known in the art, such as amplitude, pulse duration, etc. Typically a stimulation signal transmitter is constructed to produce a single or very narrow range of frequencies, of which one is selected for operation. However, in the present invention, the signal generation or transmission apparatus is capable of adjustment over a range of frequencies and pulse widths, as discussed below.

The stimulation signal frequency is chosen from those frequencies which are known to induce muscle contraction in human patients. A typical frequency range for physiologically induced muscle contraction is in the range of 10 to 100 Hertz. Therefore, for the present method, frequencies within this range are employed for maximum muscle response. The initial stimulation frequency can be set anywhere within the chosen range and depends on the type of muscle fiber being stimulated which is discussed in more detail below. The initial frequency is preferably set to begin stimulation near where the maximum muscle response occurs which is typically 50 to 60 Hertz for fast muscles and lower for slow muscles.

After the necessary oscillators, power amplifiers and associated control equipment have been assembled into a, preferably programmable, stimulation apparatus and tested, a series of transcutaneous electrodes, as known in the art, are connected between the stimulator output and the muscle region to be stimulated. The generated stimulation signals are applied through the electrode structure to the skin or tissue adjacent to the muscles.

Once the initial frequency is selected and the stimulation circuitry adjusted to that frequency, stimulation signals are sent to the muscles as in an application or stimulation step 14. Stimulation occurs for short periods on the order of 4 seconds after which no stimulation is provided for a brief period on the order of 4 to 10 seconds. This allows muscles to relax and recover from the exercise as is done for most muscle stimulation protocols.

During the stimulation step 14, the work being performed or torque exerted by the muscles during contraction is observed and recorded. This is achieved in a preferred embodiment in a measuring step 16 which coincides with the stimulation step 14 by measuring the torque produced during muscle contraction. One or more torque transducers are coupled to the body or surface tissue adjacent to the joint on which the muscles of interest insert so that torque is measured as the muscles contract and then relax. This torque is accumulated as a series of periodic torque measurements during the stimulation period. At the same time, treatment is to be suspended where work output has dropped to a predetermined low value or near-zero for at least two consecutive stimulation periods.

Alternatively, other parameters indicative of muscles performing work such as EMG signals are measured or detected using appropriate transducers and sensors known in the art. This provides a value that can also be accumulated as a series of periodic measurements during a given stimulation period.

At the end of each stimulation period a verification or check step 18 is accomplished to see if the exercise or treatment has reached a maximum length of time set by a desired treatment protocol or a significant decrease in the work of the muscles over several successive periods. A typical treatment protocol exercises a muscle for no more than about 60 minutes to avoid excessive fatigue and damage.

If the treatment is not to be terminated, a second verification or monitor step 20 determines if the treatment has just begun, in which case stimulation signals at the same frequency are again applied to the muscles. When the muscle exercise or treatment reaches the second or later stimulation periods the torque measurements are integrated over the stimulation Period in an integration step 22. This integration provides a measure of the amount of work performed by the muscles during a stimulation period.

It has been discovered that to maintain the maximum tension or force exertion by muscles during stimulation as muscles fatigue, the frequency of stimulation signals needs to be adjusted. This adjustment accounts for variations in the actual muscle properties during stimulation which has not been previously done.

It has been found that as a muscle fatigues or undergoes force exertion the frequency response of the muscle changes. That is, the frequency which produces the maximum muscle force decreases as the muscle works. There are several possible reasons for this phenomenon including the accumulation of chemical by products which alter the nature of the fiber response. Therefore, to maintain a maximum tension on the muscle or a high exertion force and work output, the present stimulation method adjusts the frequency to generate maximum muscle force by "tuning into" the maximum force generating frequency for the muscles.

At the end of each successive exercise or stimulation period or step 14, the work performed as determined by the integrand resulting from the integration step 22 is compared in a comparison step 24 to a predetermined standard. If the work output is below the standard then control circuitry directs the variable frequency stimulation signal apparatus (step 25) to decrease the frequency output by a fixed amount as in adjustment step 26. If the work output is above the standard then the variable frequency stimulation signal apparatus is directed (step 25) to increase the frequency as in adjustment step 28. The new stimulation frequency is now used to stimulate the muscles again for another stimulation period at which time the work output is again compared to the standard.

The impact of varying the frequency is that the energy coupled into the muscles is varied. An alternative method of varying the energy transferred to the muscles during stimulation is to vary the pulse width of the stimulation signals. Instead of adjusting the frequency in predetermined steps, the pulse width is adjusted in predetermined steps in response to the work output by the muscles under stimulation. In this manner the amount of energy transferred or coupled into the muscles is decreased or increased according to the work capacity of the muscles.

Figure 3A:
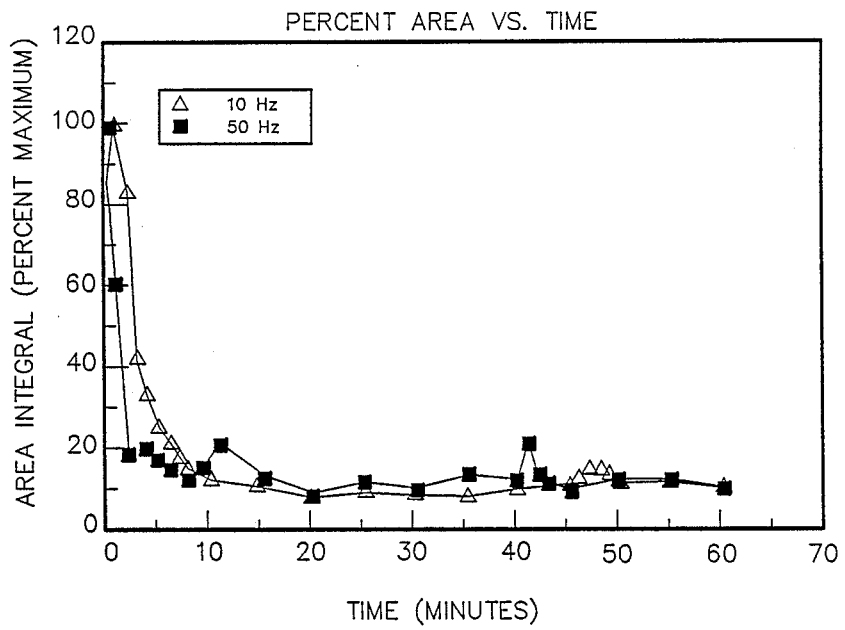
FIG. 3a is a graphic presentation of a typical variation in work over time for the method of FIG. 1 in typical muscles.
Figure 3B:
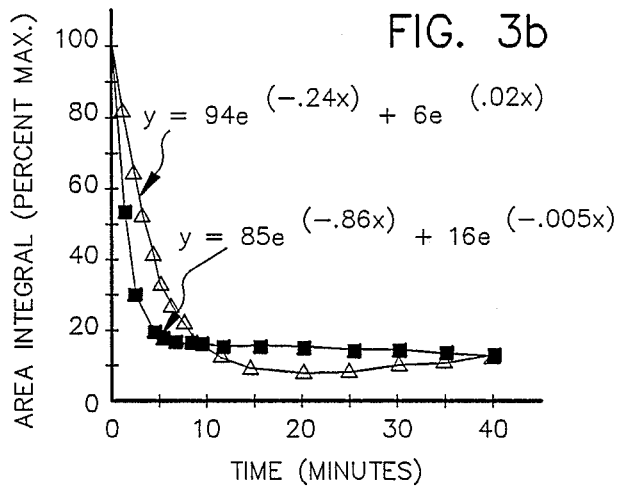

The standard work value used in the comparison step 24 can be readily derived using one of two methods. The first method is to record the work output of a muscle or set of muscles during a manually operated muscle exercise program. The frequency is varied during this program using torque readings and general physical indications of muscle performance. This exercise program can be repeated several times to provide an adequate database. This information is used to formulate an idealized frequency versus work curve for the muscles which is then used as a standard for later exercise. An example of such a curve is illustrated in FIG. 3b.

An alternative is to establish a dynamic standard by recording the work output value at the end of each exercise interval N and comparing this to a work output value previously stored for period $N-1$. The work value stored for the period $N-1$ is treated as the standard so that changes in work output over time cause the frequency to be automatically adjusted to compensate. This closed feedback loop adjustment greatly increases the long term tension and work output that can be maintained from muscles.

For example, it has been found that by using the method of the present invention, the amount of work performed by a muscle or group of muscles can be increased by a factor of at least 3. The result is a more effective exercise protocol for the muscle stimulation or exercise treatment and ultimately increased strength. In addition, this method of exercise adapts itself to the muscle properties over the long run as treatment progresses and the muscle changes.

In the prior art, there is no attempt to maximize the amount of work performed over a treatment period. That is, there is no attempt to adjust the stimulation frequency to account for the specific frequency response of muscles being stimulated. It is now known that muscle fibers and, therefore, muscles differ in terms of the frequency that induces the greatest force of contraction dependent not only on the exercise regime but the type of muscle fiber. Muscles respond more readily to stimulation in certain predetermined frequencies which range from a fast frequency on the order of 50–70 Hertz, to slower frequencies on the order of 10 Hertz. This difference in frequency response or inducement is referred to as a difference between fast and slow muscles, which generally corresponds to the faster or slower frequencies of optimum stimulation.

It is generally not as efficient to stimulate a group of muscles, as done in the prior art, using a single frequency without regard for the underlying muscle type. Therefore, in the method of the present invention, although not necessary for successful operation, the muscle type is preferably determined first and a starting stimulation frequency chosen accordingly.

Figure 2:
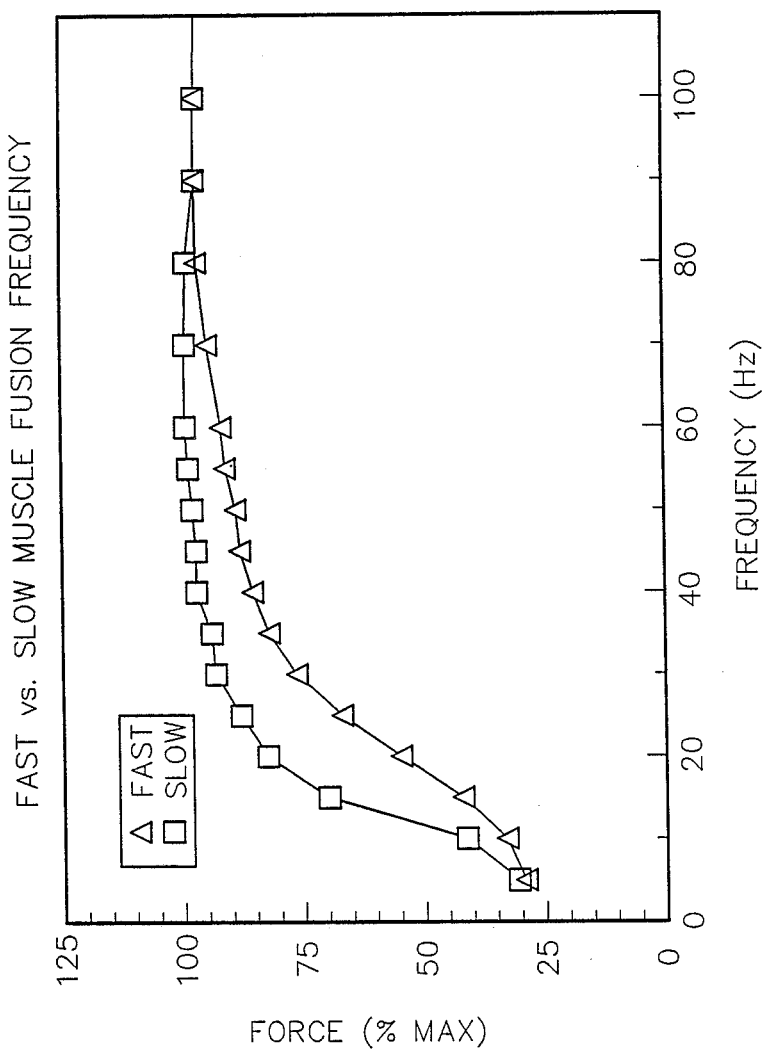
FIG. 2 illustrates a force versus frequency chart used in association with the method of FIG. 1.

This is done by first stimulating the muscle and determining the work output over a short period of time. The frequency is varied over a relatively short sampling period on the order of 20 seconds duration and the work output versus the frequency is recorded. A graphic plot of typical data for such an initial stimulation period is shown in FIG. 2. The work performed or torque exerted by the muscle is normalized to show a relative change in work versus the input stimulation frequency and to show the relative percentage of fast versus slow fibers in the muscles.

In FIG. 2, it can be seen that a frequency is reached beyond which no additional increase in work is produced for increased frequency. The frequency at which the maximum work was first achieved is recorded as the maximum stimulation frequency $f_{max}$. This value is used to set the initial stimulation frequency for the step 12. The frequency chosen typically represents the frequency needed to drive the fastest muscle fibers in the target muscle group (largest percentage composition). Once the muscle type is known a fixed frequency is chosen and applied, and the exercise treatment previously described employed.

During treatment, the work performed by the muscles, as indicated by the measured torque will decline due to muscle fatigue. The magnitude of the decline is a function of the muscle fiber composition and the stimulation frequency. If stimulation continues at the initial frequency, torque or work declines to a near-zero level. An example of this is shown in FIG. 3a where the normalized work output for a typical set of muscles undergoing stimulation is plotted versus the duration of the overall treatment, here 60 minutes. The two separate curves represent a fixed 10 Hertz stimulation frequency and a fixed 50 Hertz stimulation frequency.

Using standard "best fit" curve fitting procedures understood in the mathematical arts, the curves resulting from plotting data in FIG. 3a are approximated by the mathematical expressions shown and plotted in FIG. 3b. The equations or mathematical expressions represented by this second set of curves can then be used as a standard value for the normal work output by muscles over time at these frequencies. These equations can then be computed for comparison to the incoming integration results as the standard torque or work values previously discussed. This eliminates the storage and retrieval of large numbers of data points which otherwise make up a standard curve. This also allows more accurate synchronization of the standard value with a variety of stimulation periods or sampling intervals.

Figure 4:
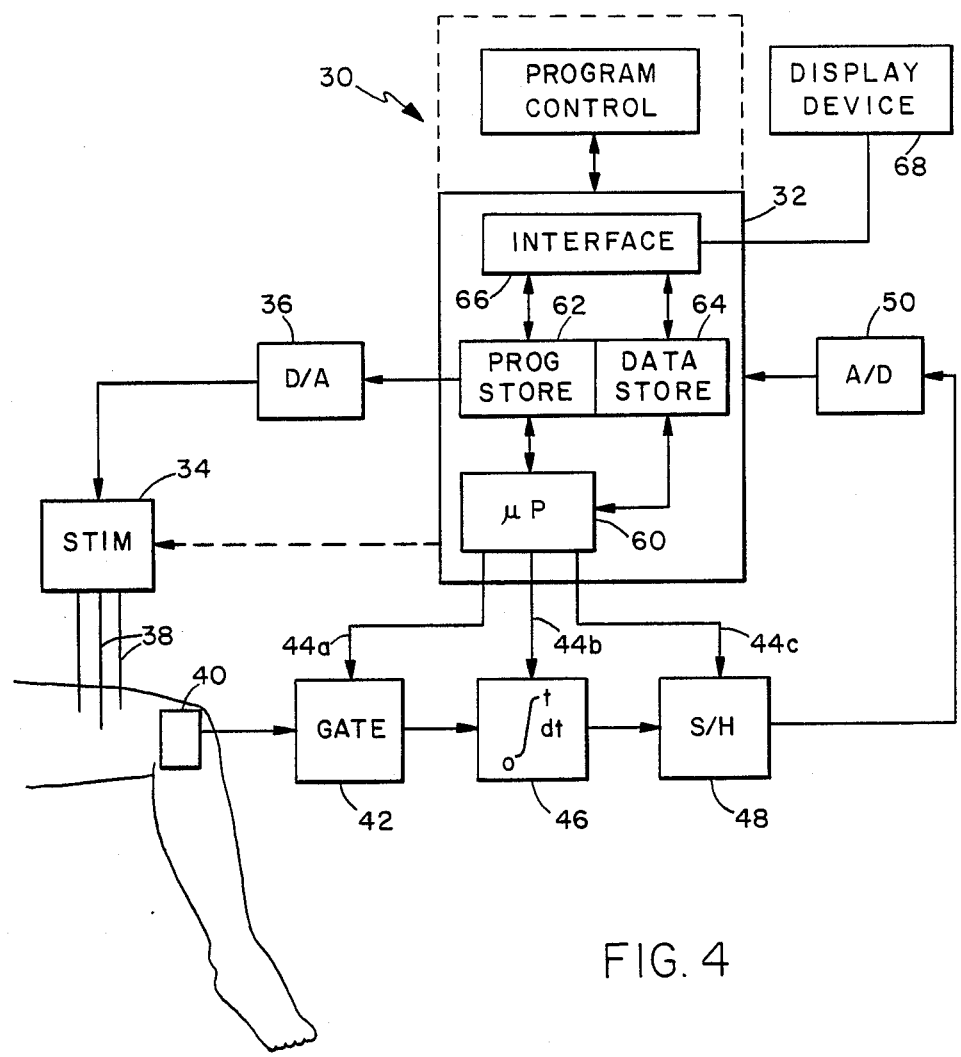
FIG. 4 illustrates in schematic form an apparatus for implementing the steps of FIG. 1.

An apparatus for realizing the steps of the present invention method is shown in FIG. 4. In FIG. 4 a muscle stimulation or exercise apparatus 30 is shown having a controller 32 which controls the operation of a stimulator 34 which provides the appropriate stimulation signals. The stimulator 34 comprises elements known in the art such as, but not limited to, power transistors, transformers, high voltage power supplies, RF isolators, etc., which form a circuit for receiving small amplitude control signals and, generating the desired stimulation signals at higher voltages. Exemplary circuitry for implementing the stimulator 34 is shown in the above described patents such as U.S. Pat. Nos. 4,499,900, 4,556,214, and 4,569,352. The stimulation signals are typically powered at voltages up to 300 volts and currents up to about 250 milliamperes.

The output of the stimulator 34 is transferred to the muscles using transcutaneous electrodes as known in the art. These electrodes can be secured in place using several methods, such as straps, adhesive tapes, or conductive suction cups. Even though the present invention works well with implanted electrodes, easily removable electrodes are preferred since the general application of the invention is for short term or transient use in exercise and not for paralyzed muscle locomotion.

The controller 32 sets the frequency, amplitude, pulse width, and duration for the stimulation signals by sending control signals to the stimulator 34. The stimulator interprets the parameters from the control signals and transmits the appropriate output stimulation signals.

A preferred embodiment for the controller 32 is a small micro- or mini-computer. However, digital electronics components in the form of integrated circuits such as a microprocessor 60 and associated support circuits including RAM, ROM or PROM forming program storage means 62 and data storage means 64, or I/0 or bus controllers forming interface circuitry 66, can be used to create a small self contained exercise controller which can be housed in a portable enclosure. The microprocessor, RAM, ROM, or EPROM components are commercially available from a number of known sources along with design guidelines and are understood in the electronics arts and are not explained in further detail here. Such a self contained controller can be battery powered and highly portable. In addition, digital processing components allow the implementation of flexible exercise protocols and work value computations which increase the usefulness of the apparatus.

The use of data storage circuitry also allows torque or work measurements to be stored along with the stimulation frequency and other information and retrieved at a later time through an interface connector or circuit 66 for future display such as by a display device 68, storage on magnetic media, or conversion to a printed chart or the like. This allows efficient monitoring of patient compliance and progress without direct personnel monitoring.

Digital control circuitry and program storage also allows control of multiple channels of stimulation signals and work performance data so that several muscles or muscle groups can be stimulated simultaneously or in a timed relationship as part of an exercise or treatment program.

When using a digital type controller 32, the frequency and amplitude information is provided as a multi-bit digital signal to the stimulator 34. Depending upon the internal circuitry of stimulator 34, i.e. analog input or digital, a Digital-to-Analog converter 36 can be used to change the output of the controller 32 to an analog signal before processing by the stimulator 34, or the digital signal can be transferred directly into the stimulator 34.

The analog stimulation signal produced by the stimulator 34 is generated at or amplified to a desired amplitude on the order of 10-30 volts. The stimulator 34 generates output signals at frequencies selected by the controller 32 in the appropriate frequency range of about 10-100 Hertz. If desired the stimulator 34 can convert signals from the controller 32, or other source, from another frequency or pulse width range to the desired frequencies. The output from the stimulator 34 is then transferred along the electrodes 38 to the muscles.

A torque measuring device or transducer 40 is coupled to the joint on which the muscles insert to determine the amount of torque exerted by the muscles during stimulation. This can be accomplished by connecting the transducer to the skin surface adjacent to the muscles and extending between opposite sides of the muscle group (lengthwise) or across related joint structures.

A variety of torque transducers 40 are known to those skilled in the art and a detailed description is not provided here. Such transducers can be secured in place using straps or similar fastening means wrapped around limbs or adhesively coupled to tissue surrounding the muscles.

The torque transducer 40 detects the force exerted by the muscles during stimulation over some predefined moment and puts out a signal proportional to the torque generated. This signal is transferred to a synchronization or gating device 42.

The synchronization device 42 comprises one of several known circuits for gating the passage of data signals and serves to control or synchronize the flow of data from the transducer 40 to subsequent processing stages so that the torque can be measured over predetermined time intervals or stimulation periods. The control means 32 provides a set/reset signal on the line 44a to allow the passage of data or reset the gate to prevent transfer.

The data or signal output from the gating device 42 is directed to an integration circuit 46 which collects and integrates the amplitude of torque over each successive stimulation time period. The integrated output of torque over the stimulation period provides a measure of the work performed by the stimulated muscles during that period.

The resultant numerical value for the integrand computed in the integrator 46 is transferred to a sample and hold circuit 48 for transfer to the controller 32 and the integrator 46 reset to zero by a signal on line 44b. The sample and hold device 48 comprises elements known in the art such as, but not limited to, integrated circuit data latches.

If the controller 32 comprises digital processing circuitry then the output of the sample and hold circuit 48 is run through an Analog-to-Digital converter 50 as it is transferred to the controller 32, and the sample and hold circuit reset by line 44c. In the alternative, the initial torque values are converted to digital form and then transferred into a digital computer type controller 32 where the signal accumulation, gating and integration are implemented within the controller 32 as software procedures.

The torque integrand value is transferred either directly, or through the sample and hold device 48 to the controller 32 where it is compared to a previously stored standard value. As discussed above, the previously stored value can arise from an idealized Curve and reiterative fitting process or from previous stimulation intervals. In either case this information can be stored in a memory storage element and recalled by the controller 32 for comparison with current values transferred from the integrator 46 and sample and hold device 48.

The new torque integrand is subtracted from the stored work performance value to determine if the work being performed by the muscles is decreasing with respect to the standard (or previous work output). At this point the controller 32 alters the frequency of the stimulation signals, through commands or signals to the stimulator 34, in predetermined steps according to the relationship between the current or new torque integrand value and the stored standard.

If the current work or torque values are lower or equal to the stored value, the frequency is decreased to allow muscle recovery from the fatigue. If the current work or torque values are higher than the stored value, the frequency is increased to cause the muscles to generate more work over the treatment interval. In this way, the muscles are caused to generate the maximum amount of work during the treatment periods without excessive fatigue.

The range of adjustment in the frequency should be relatively small, or between about 4-6 Hertz in order to readily adapt to small muscle changes. In the preferred embodiment adjustment steps of about 5 Hertz are employed. Large adjustments would tend to adapt poorly to muscle property variations and cause phenomena such as overshoot or overcompensation which make efficient tracking of muscle frequency response difficult.

As previously discussed with regard to the method of the present invention, the frequency can remain fixed while the pulse width is varied to effect varying levels of energy transfer to the muscles under stimulation. In this mode, the stimulator 34 is capable of varying the pulse width of the stimulation signals in response to commands from the controller 32. After each stimulation period the work output from the muscles is compared to the desired standard work value and the pulse width adjusted wider or narrower in response to measured increases or decreases in work output respectively. Again, the width adjustments should not exceed about 25 to 50 percent of the overall value to prevent overshoot and other associated control problems.

What has been described is a new method of controlling the work generated by muscles during functional electrical stimulation treatment or exercise to maximize the tension and improve the development of muscle strength and tone.

While the description of operation generally discussed a single muscle group and stimulation signal output channel it will be readily understood by those skilled in the art that the present invention has been explained in this manner for purposes of clarity and that one advantage of the closed loop feedback process is that multiple muscles or muscle groups can be stimulated using multiple stimulators 34 and a single programmable controller 32. An electronic controller based on the aforedescribed computer technology allows complex coordination of muscle stimulation through a variety of protocols. This provides advanced exercise protocols, possibly under patient control, while maintaining safety due to automatic monitoring of each muscle group's work output.

The foregoing description of preferred embodiments has been presented for purposes of illustration and description. It is not intended to be exhaustive nor to limit the invention to the precise form disclosed, and many modifications and variations are possible in light of the above teaching. The embodiments were chosen and described to best explain the principles of the invention and its practical application to thereby enable others skilled in the art to best utilize the invention in various embodiments and with various modifications as are suited to the particular use contemplated. It is intended that the scope of the invention be defined by the claims and their equivalents.

What I claim as my invention is:

1. A method of strengthening skeletal muscles, comprising the steps of:
   applying to said muscles a series of stimulation signals having predetermined signal characteristics comprising frequency, pulse-width, and amplitude so as to couple electrical energy into said muscles;
   measuring work output by the muscles in response to a stimulation signal over a predetermined period N;
   comparing the measured work output to a prestored work value and providing a difference therebetween; and
   adjusting the energy coupled into said muscles by adjusting signal characteristics of subsequently applied stimulation signals in response to said difference.

2. A method of strengthening skeletal muscles, comprising the steps of:
   applying a series of stimulation signals to the muscles having predetermined signal characteristics comprising frequency, pulse-width, and amplitude;
   measuring work output by said muscles in response to a stimulation signal;
   comparing the measured work output to a prestored work value and providing a difference therebetween;
   adjusting the frequency of subsequently applied stimulation signals in response to said difference; and
   returning to said measuring step.

3. The method of claim 2 wherein said step of adjusting the frequency of said stimulation signals further comprises the steps of:
   incrementing the frequency by a predetermined frequency step each time an increase in work output is measured as between adjacent periods up to a predetermined maximum frequency limit;
   decrementing said frequency by said predetermined frequency step each time a decrease in work output is measured between adjacent periods down to a predetermined minimum frequency limit.

4. The method of claim 3 wherein said predetermined frequency step is on the order of 4–6 Hertz.

5. The method of claim 3 wherein:
   said stimulation signal has a frequency varying over about a 10–100 Hertz frequency range applied to said muscles for an initial stimulation period;
   said torque is generated by said muscles during said initial period; and
   said maximum frequency limit is set equal to a frequency within said range for which said torque has a maximum value.

6. The method of claim 3 further comprising the steps of:
   applying a stimulation signal having a frequency varying over about a 10–100 Hertz frequency range to said muscles for an initial stimulation period;
   measuring the EMG generated by said muscles during said initial period; and
   setting said maximum frequency limit equal to a frequency within said range for which said EMG has a maximum value.

7. A method of strengthening skeletal muscles through maximizing muscle tension, comprising the steps of:
   applying a series of stimulation signals to the muscles having predetermined signal characteristics comprising frequency, pulse-width, and amplitude;
   measuring work output by said muscles in response to a stimulation signal;
   comparing the measured work output to a prestored work value and providing a difference therebetween; and
   adjusting the pulse width of subsequently applied stimulation signals in response to said difference.

8. The method of claim 1 wherein said step of applying stimulation signals to said muscles further comprises generating stimulation signals at a frequency in the range of about 10 to 100 Hertz.

9. The method of claim 1 wherein said step of measuring the work output comprises the steps of:
   measuring torque generated by said muscles during stimulation; and
   integrating said torque over a predetermined time interval to produce a measured work value.

10. The method of claim 9 further comprising the step of storing a precomputed work value as said prestored work value.

11. The method of claim 9 further comprising the steps of:
    measuring torque generated by said muscles during stimulation during a predefined period N−1;
    integrating said torque over said period N−1;
    storing results of said integrating step as said prestored work value; and
    comparing said measured work output for the period N to said prestored work value for the period N−1.

12. The method of claim 1 wherein said step of measuring the work output comprises the steps of:
    measuring electromyogram (EMG) output generated by said muscles during stimulation; and
    integrating said EMG over a predetermined time interval to produce a measured work value.

13. The method of claim 12 further comprising the step of storing a precomputed work value as said prestored work value.

14. The method of claim 12 further comprising the steps of:
   measuring EMG generated by said muscles during stimulation during a predefined period N−1;
   integrating said EMG over said period N−1;
   storing results of said integrating step as said prestored work value; and
   comparing said measured work output for the period N to said prestored work value for the period N−1.

15. The method of claim 1 further comprising the steps of:
   storing measurements of work output in a data storage element;
   storing frequency of stimulation corresponding to said measurements of work output in a second data storage element; and
   transferring said stored work output and frequency data to a data display.

16. An apparatus for exercising skeletal muscles through obtaining maximum tension, comprising:
   at least one electrode adapted to be electrically coupled to said muscles;
   at least one stimulation means connected to said electrode for coupling electrical energy into said muscles by generating electrical stimulation signals having predetermined characteristics comprising frequency, pulse-width, and amplitude to which the muscles are responsive;
   work detection means adapted to be operatively coupled to said muscles for measuring work output by said muscles during stimulation;
   comparison means connected to said work detection means for comparing said work measured with a prestored work value and for providing a difference therebetween; and
   adjustment means connected to said comparison means and said stimulation means for adjusting the signal characteristics of said stimulation signals and incrementing and decrementing the electrical energy adapted to be coupled into the muscles by said stimulation signals in response to decreases and increases respectively in said difference.

17. The apparatus of claim 16 wherein said adjustment means further comprises frequency adjustment means for incrementing and decrementing the frequency of stimulation signals in response to decreases and increases respectively in said difference.

18. The apparatus of claim 17 wherein said frequency adjustment means comprises:
   a torque transducer adapted to be coupled to body surfaces adjacent said muscles for generating an output signal proportional to a torque exerted during motion of said muscles;
   synchronization means connected in series with said torque transducer for gating the output signal of said transducer at predetermined time intervals; and
   integration means connected in series with said synchronization means for receiving transducer output signals over a predetermined time interval and integrating a magnitude thereof over that interval so as to produce an integrand representative of work exerted by said muscles; and
   input means for transferring the integrand to said comparison means.

19. The apparatus of claim 17 wherein said frequency adjustment means comprises:
   an EMG transducer adapted to be coupled to body surfaces adjacent said muscles for generating an output signal proportional to a torque exerted during motion of said muscles;
   synchronization means connected in series with said torque transducer for gating the output signal of said transducer at predetermined time intervals; and
   integration means connected in series with said synchronization means for receiving transducer output signals over a predetermined time interval and integrating a magnitude thereof over that interval so as to produce an integrand representative of work exerted by said muscles; and
   input means for transferring the integrand to said comparison means.

20. The apparatus of claim 18 wherein said control means comprises a portable programmable microprocessor device which further comprises:
   a central processing unit for controlling the transfer of data and stimulation signal characteristics in response to input commands and for computing a difference between prestored work values and measured work values;
   data storage means connected to said work detection means and said central processing unit for storing measured work values;
   program storage means connected to said central processing unit for storing commands used for setting signal characteristics in said central processing means, for computing said difference in work output, and for terminating exercise; and
   input/output control means connected to said central processing unit for transferring stimulation characteristic data and measured work values into said microprocessor device and for transferring signal control parameters from said microprocessor device to said stimulation means stimulator.

21. The apparatus of claim 20 further comprising data transfer means connected to said data storage means for retrieving stored measured work data and stimulation frequency values stored in said microprocessor device and for transferring same to other apparatus for analysis and display.

22. The apparatus of claim 16 wherein said adjustment means further comprises pulse adjustment means for incrementing and decrementing a pulse width of said stimulation signals in response to measured decreases and increases respectively in the measured work.

23. The apparatus of claim 22 wherein said pulse adjustment means further comprises:
   a torque transducer adapted to be coupled to body surfaces adjacent said muscles for generating an output signal proportional to a torque exerted during motion of said muscles;
   synchronization means connected in series with said torque transducer for gating the output signal of said transducer at predetermined time intervals; and
   integration means connected in series with said synchronization means for receiving transducer output signals over a predetermined time interval and integrating a magnitude thereof over that interval so as to produce an integrand representative of work exerted by said muscles; and
   input means for transferring the integrand to said comparison means.

24. The apparatus of claim 22 wherein said pulse adjustment means further comprises:
an EMG transducer adapted to be coupled to body surfaces adjacent said muscles for generating an output signal proportional to a torque exerted during motion of said muscles;
synchronization means connected in series with said torque transducer for gating the output signal of said transducer at predetermined time intervals; and
integration means connected in series with said synchronization means for receiving transducer output signals over a predetermined time interval and integrating a magnitude thereof over that interval so as to produce an integrand representative of work exerted by said muscles; and
input means for transferring the integrand to said comparison means.

* * * * *